Figure 1:
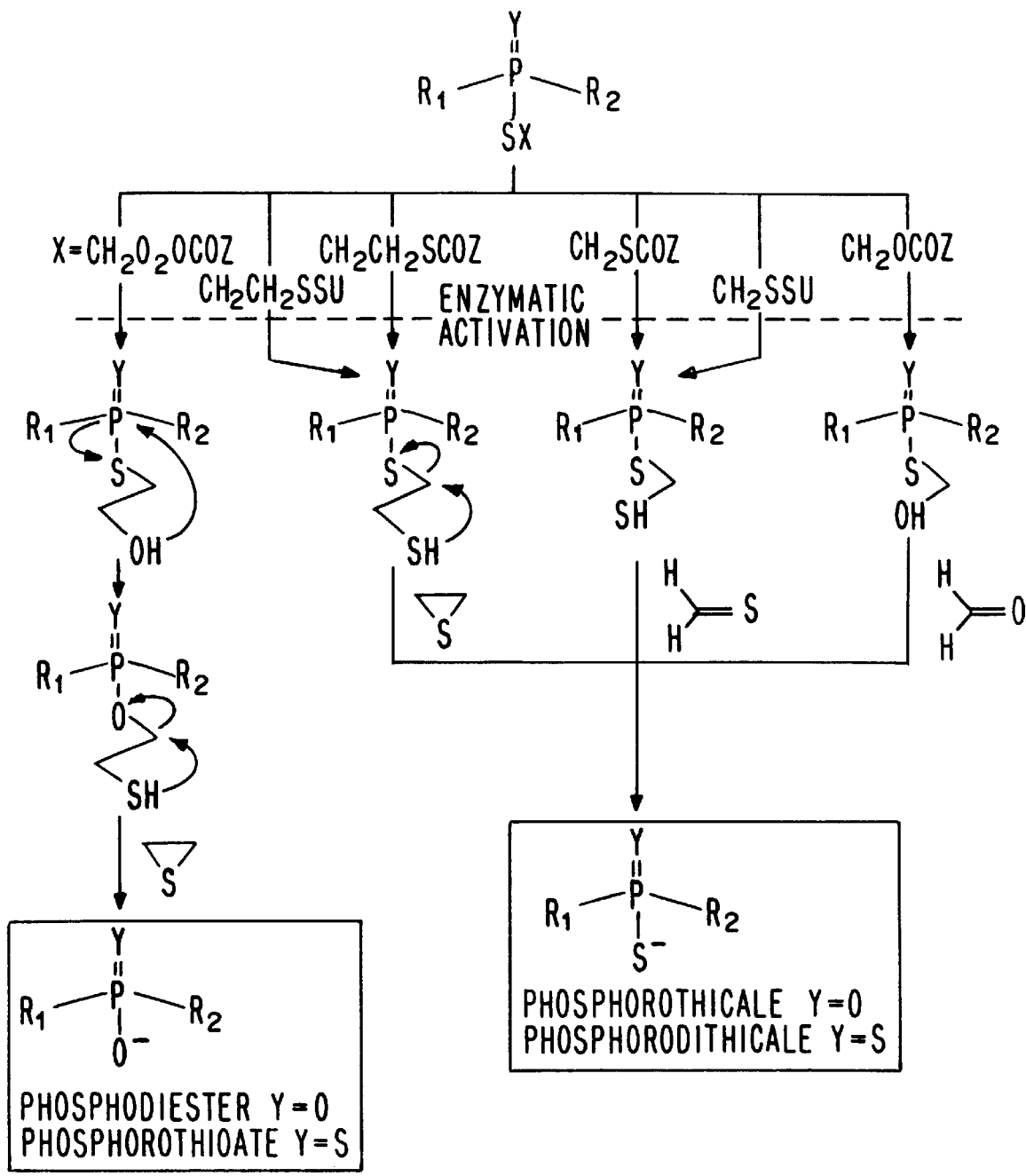

United States Patent [19]

Imbach et al.

[11] Patent Number: 5,770,713
[45] Date of Patent: Jun. 23, 1998

[54] PHOSPHOROTHIOATE TRIESTER OLIGONUCLEOTIDES AND METHOD OF PREPARATION

[75] Inventors: Jean-Louis Imbach; Bernard Rayner, both of Montpellier, France

[73] Assignee: Centre National de la Recherche Scientifique, Cedex, France

[21] Appl. No.: 545,785

[22] PCT Filed: May 11, 1994

[86] PCT No.: PCT/FR94/00563

§ 371 Date: Jan. 17, 1996

§ 102(e) Date: Jan. 17, 1996

[87] PCT Pub. No.: WO94/26764

PCT Pub. Date: Nov. 24, 1994

[30] Foreign Application Priority Data

May 12, 1993 [FR] France ................................ 93 05706

[51] Int. Cl.$^6$ .............................. C12Q 1/68; C07H 19/00; C07H 21/02; C07H 21/04
[52] U.S. Cl. .......................... 536/22.1; 435/6; 536/23.1; 536/25.3; 536/25.33
[58] Field of Search .............................. 435/6; 536/22.1, 536/23.1, 25.3, 25.33

[56] References Cited

U.S. PATENT DOCUMENTS 5,210,264   5/1993   Yau ........................................ 558/167

FOREIGN PATENT DOCUMENTS 0463712   1/1992   European Pat. Off. .
0519463   12/1992  European Pat. Off. .
WO 91/04983 4/1991   WIPO .

OTHER PUBLICATIONS

Marshall et al. "Phosphorodithioate DNA as a Potential Therapeutic Drug" Science, vol. 259, pp. 1564–1570, Mar. 1993.

Primary Examiner—Ardin H. Marschel
Assistant Examiner—Jezia Riley
Attorney, Agent, or Firm—Woodcock Washburn Kurtz Mackiewicz & Norris LLP

[57] ABSTRACT

The trister phosphorothioate oligonucleotides disclosed comprise internucleotide concatenations having a P—S⁻ bond protected by a bioreversible grouping (X) in intracellular media.

35 Claims, 1 Drawing Sheet

PHOSPHOROTHIOATE TRIESTER OLIGONUCLEOTIDES AND METHOD OF PREPARATION

The present invention relates to phosphorothioate triester oligonucleotide compounds and to a method of preparation.

In the present application, the term "oligonucleotides" generally speaking indicates a DNA or RNA polynucleotide, that is to say one in the ribo- (RNA) or deoxyribo- (DNA), or even mixed ribo-deoxyribo, series. These oligonucleotides are in general formed by a linkage of 2 to 100 nucleotides, and more generally, of 5 to 50 nucleotides.

These oligonucleotides are used for biological or therapeutic purposes according to different approaches: antisense (formation of duplex), anti-gene (formation of triple helixes), catalytic (RNA with ribozyme activity) or sense (protein target).

The antisense oligonucleotides are short synthetic DNA or RNA or mixed molecules of complementary sequences to a target sequence belonging to a gene or to an RNA messenger whose expression it is specifically desired to block. The antisense oligonucleotides are in fact directed against a messenger RNA sequence, or alternatively against a DNA sequence and hybridize to the sequence to which they are complementary, thus being able to block genetic expression.

The antisense deoxyribonucleotides can also be directed against certain bicatenary DNA regions (homopurine/homopyrimidine sequences or sequences rich in purines/pyrimidines) and thus form triple helixes. These oligonucleotides directed in this way against DNA have been called "anti-gene" or alternatively "anti-code". The formation of a triple helix, at a particular sequence, can block the fixing of proteins intervening in the expression of a gene and/or allow irreversible damage to be introduced into the DNA if the oligonucleotide under consideration possesses a particular reactive group. Such antisense oligonucleotides can form artificial restriction endonucleases, directed against specific sequences.

In cells, and more particularly in an organism, in the blood circulation, for example, the natural oligonucleotides are sensitive to degradation by nucleases. Nucleases are degradation enzymes capable of cutting the phosphodiester bonds of DNA or of RNA, either by introducing internal cleavages into mono- or bicatenary molecules, or by attacking these molecules starting from their ends. The enzymes which attack internally are called endonucleases and those attacking by the ends are called exonucleases.

The use of oligonucleotides encounters two major problems which are, on the one hand, great sensitivity to degradation by exonucleases which are found as well in the serum or in extracellular medium or in intracellular cytoplasmic medium and, on the other hand, low intra-cellular penetration.

The use of modified oligonucleotides has already been proposed to increase the stability of oligonucleotides or favor penetration through cellular membranes or alternatively to stabilize hybridization and specific affinity for a target sequence, whether this be a single or double strand nucleic acid, or even a protein, or alternatively to increase the interaction with said target sequence. Chemical modifications of the structural skeleton of the molecule or derivations or couplings to reactive or intercalating groups have been proposed, in general localized at the end of the oligonucleotides.

As far as the chemical modifications of the skeleton are concerned, it has been proposed to modify the nature of the internucleotide phosphate linkage, especially in the form of methylphosphonate, phosphorothioate or phosphorodithioate; or alternatively by modifying the sugar part, especially by an alpha-anomeric configuration, a 2'—O—CH$_3$ substitution or by replacing the oxygen of the furan ring by a sulfur (4'-thioribonucleotide). It has also been proposed to modify the nucleotide bases.

Thus, in French Patent Applications FR 83 01223 (2 540 122) and FR 84 11795 (2 568 254) chemical compounds formed by an oligonucleotide including natural or modified linkage of β-nucleotides have been described, on which are found, fixed by a covalent bond, at least one intercalating group, which compounds have the property of selectively blocking the expression of a gene and which therefore are particularly useful in therapy as antiviral, antibiotic, antiparasitic or antitumor substances.

In International Application WO 88/04301, oligonucleotides of alpha-anomeric configuration have been described having more stable parallel pairings with complementary sequences.

However, the uses proposed until now raise other problems, especially of toxicity, as chemical modification introduced into the molecule prove to be capable of inducing toxicity on the pharmacological level in certain therapeutic applications. Generally speaking, it is difficult to combine the different criteria of resistance to nucleases, stabilization of hybridization, penetration into the cell and, likewise, increase in activity yielding the duplex with the RNAse H substrate complementary target sequence, which has the property of cleaving the DNA/RNA duplexes.

The oligonucleotide compounds whose phosphate part was modified by methylphosphonate are particularly resistant to degradation by nucleases. However, the electrically neutral oligomers such as the oligomers of the methylphosphonate type penetrate more easily into the cell than the electrically charged oligomers such as the phosphodiesters. However, these methylphosphonate derivatives have a chirality, especially at the phosphate, thus leading to the formation of diastereoisomers. In addition, the RNA/oligodeoxynucleotide methylphosphonate duplexes are not substrates of RNAseH. The oligomer derivatives of the phosphorothioate diester type have a resistance to degradation by nucleases but to a lesser degree than the methylphosphonate oligomers. On the other hand, they lead to electrically charged oligomers capable of activating RNAse H, but penetrate less easily into the cell than the methylphosphonate oligomers.

Generally speaking, the oligonucleotides which are the subject of the invention are intended to provide novel stable oligonucleotides capable of being internalized in cells and capable of hybridizing and/or of having an affinity for specific nucleic acid or protein sequences and thus of interacting with cellular or viral factors.

The present invention provides oligonucleotides with electrically neutral phosphorothioate triester linkages being able to re-form, after penetration into the cell, and selectively, phophorothioate diester or polar phosphodiester bonds. Analogously, the present invention includes phosphorodithioate triester linkages giving, intracellularly, phosphorodithioate diester or phosphorothioate diester linkages.

To do this, P—S⁻ bonds of an oligomer are selectively protected by a bioreversible group (X) in the intracellular media.

The modifications proposed according to the invention produce oligomers having the advantageous properties of phosphorothioate diester derivatives, while overcoming the disadvantages of the latter, especially as far as their sensitivity to extracellular exonucleases and their difficulty in penetrating through the cellular membrane is concerned.

The present invention thus relates more precisely to a phosphorothioate or phosphorodithioate triester oligonucleotide, characterized in that it comprises internucleotide linkages which have a P—S⁻ bond protected by a bioreversible group (X) in intracellular media.

The route of synthesis used in this invention consists in the use of a nucleophilic substitution reaction by the sulfur atom of the P—S⁻ bond of an alkylating agent XL, L being a leaving group (halogen, ester, tosyl . . . ) and X a bioreversible group. It follows that it is possible to convert the P—S⁻ functions into corresponding bioreversible phosphotriesters, as will be shown in the examples below.

Such a process does not require protection of heterocyclic bases and can therefore be carried out directly on a previously prepared oligonucleotide. It is thus possible to obtain phosphorothioate triester oligomers starting from phosphorothioate diester oligomers. In fact, a mixed linkage comprising phosphodiester (P—O⁻) and phosphorothioate (P—S⁻) bonds will be selectively alkylated at the sulfur atoms.

The phosphorothioate triester oligomers according to the present invention are electrically neutral in the extracellular medium and therefore benefit from improved penetration into the cell. In addition, they allow electrically charged phosphodiester or phosphorothioate diester oligonucleotides to be delivered intracellularly which are capable, as such, of being substrates of RNAse H when they form a mixed RNA/DNA duplex with their target complementary sequences.

The principle of the invention applies to any synthetic oligonucleotide, of the DNA, RNA or mixed series, whatever the biological target envisaged, insofar as it has internucleotide linkages containing a P—S⁻ bond capable of being alkylated by bioreversible groups.

In one embodiment, the oligonucleotides according to the present invention correspond to the formula

(I)

in which:

Y is O or S $R_1$ and $R_2$ are respectively a residue in the 3'-O and 5'-O positions of a nucleoside or of an oligonucleotide the internucleotide linkage of which is natural or modified, the linkage of which is especially of the phosphorothioate triester type of formula

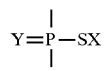

X is a —$(CH_2)_n$—$Y^1$—W radical or

X is a —$(CH_2)_n$—$Y^1$—W radical or $y^1$ is S or O n varies from 1 to 6

W is:

either SU with U being an optionally substituted alkyl, aryl or oside radical, or

with $y^2$ being O or S, and Z being an optionally substituted alkyl, aryl or oside radical.

"Modified oligonucleotide" is understood here to mean modifications in the sugar part, in the base or alternatively in the phosphate linkage, or even in the anomeric configuration of the linkages. These X groups undergo an enzymatic cleavage of the $Y_1$/W bond by the enzymatic activation of intracellular enzymes according to a mechanism illustrated in FIG. 1.

When U and Z are an alkyl, aryl or oside radical, the $C_1$ and $C_7$ alkyl radicals, benzyl and phenyl radicals and, as sugars, glucose, mannose or rhamnose are mentioned in particular.

Among these X groups, —$(CH_2)_n$—S—S—U or

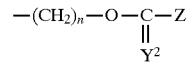

are more particularly mentioned and more particularly still

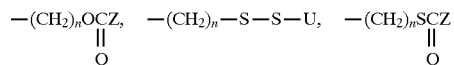

where n=1 or 2.

These phosphorothioate triester linkages are converted under the influence of intracellular enzymes either into phosphodiesters or into phosphorothioate diesters, as is shown by the decomposition studies on cellular extracts presented below and the mechanisms indicated in FIG. 1.

Among the alkyls forming the groups U or Z, the lower alkyls optionally substituted by a group chosen particular.

Thus, in a particular embodiment of the invenvention, X is —$(CH_2)_n$—S—S—$(CH_2)_{n^1}$—$X^1$ with n and $n^1$ being an integer from 1 to 4, preferably 2, and $X^1$ is H, OH, SH or $NH_2$, or X is —$(CH_2)_n$—$Y^1$—CO—Z, where n=1 or 2 and Z=$CH_3$ or tBu. More particularly still X =tBu $COOCH_2$—, $CH_3COSHCH_2CH_2$—or $CH_3COSCH_2$—.

The electrically charged phosphorothioate diester oligomers are somewhat insensitive to intracellular nuclease degradation. This is why, in an advantageous embodiment according to the invention, the oligonucleotides tides will be formed by a chimeric oligomer comprising a central DNA or RNA sequence, the internucleotide linkages of which contain a

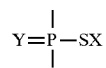

bond, this central sequence being flanked in the 5' and 3' positions by DNA or RNA sequences modified so that they are resistant to nucleases and/or stabilize hybridization with a complementary strand.

This embodiment is particularly advantageous in the case of an anti-sense approach in which an oligonucleotides nucleotide of the DNA type is used so as to form a DNA/RNA duplex which will thus be a substrate of RNAse H. These chimeric oligomers according to the invention combine all the advantageous properties of cellular penetration, resistance to intra- and extracellular enzymes and formation of duplex substrates of RNAse H.

In particular, compounds of formula I will be used in which $R_1$, and $R_2$ have sequences at the 5' and 3' ends with electrically neutral internucleotide linkages which are resistant to degradation by extra- and intra-cellular nucleases, such as linkages of the methyl-phosphonate type.

According to another embodiment, the oligonucleotide according to the invention are formed from a chimeric oligomer comprising a β-anomeric central DNA or RNA sequence, the internucleotide linkages of which are of the type Y=P-SX, this central sequence being flanked in the 5' and 3' positions by alpha-anomeric DNA or RNA sequences.

In particular, an oligonucleotide according to the invention can be formed from a chimeric oligomer containing a central sequence of phosphorothioate triester β-nucleoside linkage with internucleotide linkage of the

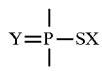

type surrounded by flanks formed from sequences of phosphate diester form alpha-nucleoside linkages.

Generally speaking, different nucleotides can be part of the formulation of oligonucleotides according to the invention. The oligonucleotides to which the present invention relates can be formed by a sequence of nucleotide bases including adenine (A), guanine (G), cytosine (C), thymine (T) and uracil (U), or the oligonucleotides can likewise include rare nucleotides (inosine, I, or rI, for example) or modified nucleotides, either in the deoxyribo- series or in the ribo- series, interconnected by non-modified or modified phosphodiester bonds according to the present invention.

In particular, the oligonucleotides can include reactive nucleotides capable of establishing bonds with the sequence of the target molecule complementary to the oligonucleotide.

Thus, the oligonucleotides according to the invention can carry reactive groups grafted onto the nucleotides, such as, for example psoralen groups, or other bridging agents or intercalating agents able to react with the sequence of the target molecule complementary to the oligonucleotide.

Likewise oligonucleotides form part of the invention, which are coupled to molecules allowing their intracellular penetration to be increased, and in particular lipophilic groups, polypeptides or proteins.

The oligonucleotides according to the invention are prepared starting from an oligonucleotide having phosphothioate diester internucleotide linkages of the type

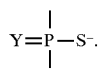

A nucleophilic substitution reaction by the sulfur atom of the —P—S⁻ bond of said phosphorothioate diester linkages is carried out on an alkylating agent XL, thus leading to the formation of an oligonucleotide with phosphorothioate triester linkages

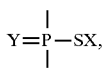

L being a leaving group such as halogen, ester or tosyl, and X being a bioreversible group according to the invention.

The phosphorothioate diester oligonucleotides with a

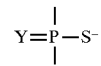

linkage are prepared by conventional methods of synthesis, by a chemical or biochemical route, or by approaches calling for combinations of chemical synthesis and molecular biology techniques.

Among the methods described as conventional, various methods of chemical synthesis of oligonucleotides have been developed and are well known to the specialists working in these fields. For example, one method consists in using a solid support called CPG (controlled pore glass) to which the first nucleotide is fixed covalently by a spacer through its 3' OH end. The 5' OH end of the nucleoside is protected by an acid-label di-p-methoxytrityl group. This approach, using phosphite triester chemistry, and in which deoxynucleoside 3'-phosphoramidite are used as synthons is called the phosphoramidite method. This approach is most used at present and has the advantage of being entirely automatic.

Another approach used for the synthesis of oligonucleotides is that of phosphonate chemistry. This approach starts with the condensation of a deoxynucleoside 3'-H-phosphonate with a deoxynucleoside coupled to a glass or silica support. Successive condensation cycles lead to the synthesis of oligonucleotide H-phosphonates. These oligonucleotides are oxidized in one step to give the phosphodiesters.

Using one or the other of these techniques, or any other sequential procedure allowing the synthesis of polynucleotide chains of determined sequence in advance, oligonucleotides having the desired starting structure are obtained.

Detailed syntheses of phosphorothioate diester oligonucleotides have been described, for example, in J. Am. Chem. Soc. 106: 6077–6079 (1984) and Nucleic Acids Res. 14: 5399–5407 (1986).

The oligonucleotides can be used as various diagnostic, cosmetic or pharmacological compositions at variable concentrations and with the appropriate excipients according to the applications.

Other characteristics and advantages of the present invention will appear in the light of the examples which follow.

FIG. 1 shows the mechanisms of intracellular decomposition of bioreversible groups.

I—Examples 1 to 3: Synthesis of phosphorothioate triester dinucleosides 4a, 4b, and 4c and evaluation of their stability in biological medium I-1—Synthesis of the compounds 4a, 4b and 4c General conditions Thin-layer chromatography (TLC) is carried out on Merck 60 $F_{254}$ silica gel sheets. The products are detected with a UV lamp (254 nm) and visualized by heating after spraying with 10% sulfuric acid in 95° ethanol. Chromatography on a silica gel column is carried out with silica Kieselgel 60 (40 μm–63 μm).

Proton NMR spectra are recorded at ambient temperature on a Brüker AC 250 apparatus. The samples are solubilized in DMSO-$d_6$. The chemical shifts (δ) are expressed in ppm with reference to the signal of DMSO-$d_5$ fixed at 2.49 ppm, taken as internal reference. The coupling constants are given in Hertz. The multiplicity of the signals observed is indicated by a small letter:

m: multiplet; pq: pseudo-quartet, t: triplet; d: doublet; s: singlet; sl: broad singlet The nucleoside having its 5' OH function free is represented sented by $N_1$ and the nucleoside having its 3' OH function free is represented by $N_2$.

The phosphorus NMR spectra are recorded at ambient temperature on a Brüker WP 200 SY apparatus with proton decoupling. The samples are solubilized in $CD_3CN$ or in DMSO-$d_6$. The chemical shifts are expressed in ppm in relation to 66% $H_3PO_4$ taken as external reference.

The mass spectra are carried out on a JEOL JMS DX 300 apparatus by the FAB ionization method in positive mode with different matrices: glycerol (G), glycerol/-thioglycerol (GT) or 3-nitrobenzyl alcohol (NBA).

The acetonitrile was distilled after heating to reflux for one night over calcium hydride and is kept over molecular sieve (4A).

The alkylating agents were synthesized according to processes described in the literature:

pivaloyloxymethyl iodide: European Patent Appl. No. 843080672 bromoethylacetyl sulfide: P. Nylen, A. Olsen, *Svensk Kem. Tid.*, 53, 274 (1941)

bromomethylacetyl sulfide: G. K. Farrington, A. Kumar, F. C. Wedler, *Oppi briefs*, 21, 390 (1989).

The phosphorothioate diester dinucleosides were synthesized according to conventional methods described in the literature, using H-phosphonate chemistry (J. Stawinski, M. Thelin, *Nucleosides and Nucleotides*, 9, 129 (1990), P.J. Garegg, T. Regberg, J. Stawinsky, R. Strömberg, *Nucleosides and Nucleotides*, 6, 655 (1987)).

Aqueous solutions of 1M and 0.5M triethylammonium hydrogen carbonate (TEAB) were used to neutralize the reaction media and to carry out the extractions.

Before lyophilization, the solutions are filtered on a Millex HV-4 filter (Millipore, 0.45 μm).

Synthesis:

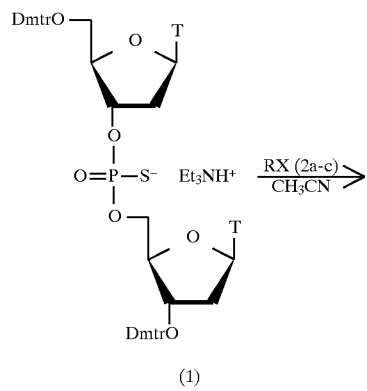

(1)

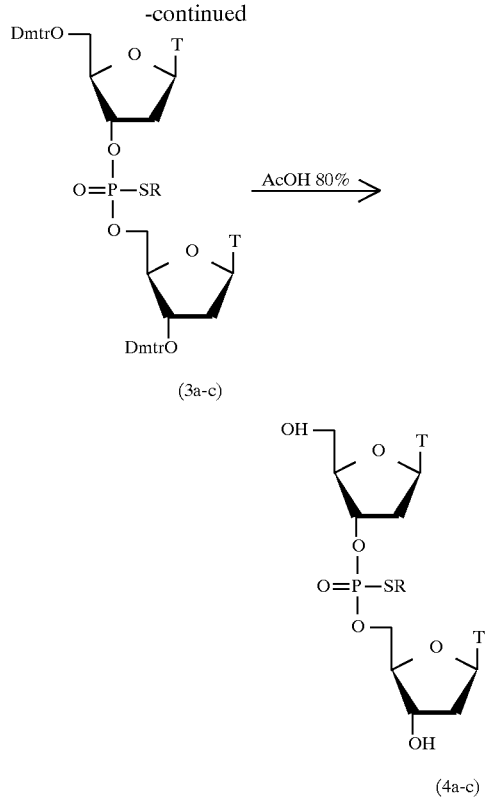

(3a-c)

(4a-c)

a: R = tBuCOOCH$_2$—; b, d: R = CH$_3$COSCH$_2$CH$_2$—;

c: R = CH$_3$COSCH$_2$— X = I (a, c et d): Br (b)

EXAMPLE 1

O-[5'-O-(4,4'-Dimethoxytrityl) thymidin-3'yl] O-[3'-O-(4,4'-dimethoxytrityl)thymidin-5'-yl] S-(pivaloyloxymethyl) phosphorothioate (3a)

Pivaloyloxymethyl iodide (2a) (484 mg, 2 mmol) is added to a solution of phosphorothioate diester dinucleoside (1) (254 mg; 0.2 mmol) in anhydrous acetonitrile (10 ml). The reaction is stirred at ambient temperature for 30 minutes, then the reaction medium is neutralized by addition of an aqueous solution of 1M TEAB (2 ml) and left for 5 minutes with stirring. The reaction mixture is then poured onto an aqueous solution of 0.5M TEAB (50 ml) and extracted with dichloromethane (3×30 ml). The organic phases are collected, washed with water (50 ml), dried over sodium sulfate, filtered and then evaporated to dryness. The residue is then chromatographed graphed on a silica gel column using a gradient of methanol (0 to 2%) in dichloromethane as eluent. The fractions containing (3a) are combined and concentrated under reduced pressure, leading to a white solid residue (220 mg; 86%) which is carefully dried for use in the following step.

$R_f$=0.67 (CH$_2$Cl$_2$/MeOH: 9/1).

O-(Thymidin-3'-yl) O-(thymidin-5'-yl) S-(pivaloyloxymethyl) phosphorothioate (4a)

The totally protected dimeric phosphorothioate triester (3a) is dissolved in a mixture of acetic acid/water/methanol (8:1:1, v:v:v) (10 ml). The reaction is left with stirring at ambient temperature for 5 hours. The reaction medium is then evaporated and the residue is coevaporated several times with water and toluene. The residue is then chromatographed on a silica gel column using a gradient of methanol (0 to 10%) in dichloro-methane as eluent. The fractions containing the product (4a) are collected, concentrated under reduced pressure, and then the residue is coevaporated several times with dioxane and lyophilized in dioxane. (4a) is obtained in the form of a white powder (98 mg, 85%).

$R_f$=0.2 ($CH_2Cl_2$/MeOH: 9/1); MS: FAB>0 (NBA): 677: $(M+H)^+$; 551: $(M-B)^+$; 424: $(M- (2B+2H))^+$; $^{31}P$ NMR ($CD_3CN$): δ=27.21 and 27.31 ppm (2 diastereoisomers); $^1H$ NMR (DMSO-$d_6$): δ=11.34 (sl. 2H, 2NH); 7.68 and 7.48 (2m, 2H, $2H_6$); 6.21 (m, 2H, $2H_{1'}$); 5.48 (d, 1H, $OH_{3'}$, J=4.4 Hz); 5.41 (d, 2H, $SCH_2O$, J=20 Hz); 5.26 (t, 1H, $OH_{5'}$, J=5.1 Hz), 5.10 (m, 1H, $H_{3'}$ ($N_1$)); 4.26 (m, 3H, $H_{3'}$ ($N_2$), $H_{5'}$ and $H_{5''}$ ($N_2$)); 4.12 (m, 1H, $H_{4'}$ ($N_1$)); 3.96 (m, 1H, $H_{4'}$ ($N_2$)); 3.61 (m, 2H, $H_{5'}$ and $H_{5''}$ ($N_1$)); 2.38 (m, 2H, $H_{2'}$ and $H_{2''}$ ($N_1$)); 2.14 (m, 2H, $H_{2'}$ and $H_{2''}$ ($N_2$)); 1.79 and 1.77 (2s, $2CH_3$ ($N_1$ and $N_2$)); 1.13 (d, 9H, $(CH_3)_3C$) ppm.

EXAMPLE 2

O-[5'-O-(4,4'-Dimethoxytrityl)thymidin-3'-yl]O- [3'-O- (4,4'-dimethoxytrityl) thymidin-5'-yl] S-(acetylthioethyl) phosphorothioate (3b)

Bromoethylacetyl sulfide (2b) (360 mg; 1.97 mmol) is added to a solution of phosphorothioate diester dinucleoside (1) (50 mg; 0.0394 mmol) in anhydrous acetonitrile (5 ml). The reaction mixture is stirred at ambient temperature for 5 days, then it is neutralized by addition of an aqueous solution of 1M TEAB (1 ml) and left with stirrring for 5 minutes. The reaction mixture is then poured onto an aqueous solution of 0.5M TEAB (25 ml) and extracted with dichloromethane (3×15 ml). The organic phases are collected, washed with water (25 ml), dried over sodium sulfate, filtered and then evaporated to dryness. The residue is then chromatographed graphed on a column of silica gel using a gradient of methanol (0 to 4%) in dichloromethane as eluent. (3b) is obtained in the form of a white solid (27 mg, 55%).

$R_f$=0.75 ($CH_2Cl_2$/MeOH: 9/1).

O- (Thymidin-3'-yl) O- (thymidin-5'-yl) S-(acetylthioethyl) phosphorothioate (4b)

The totally protected phosphorothioate triester dinucleoside (3b) is dissolved in an acetic acid/water/ methanol mixture (8:1:1, v:v:v) (5 ml) and left with stirring all night. The following day, the reaction mixture is evaporated and the residue is coevaporated several times with water and then with toluene. The solid residue is then chromatographed on a column of silica gel using a gradient of methanol (0 to 10%) in dichloro methane as eluent. The fractions containing the detritylated phosphorothioate triester dinucleoside (4b) are collected and evaporated under reduced pressure, then the residue is coevaporated with dioxane and lyophilized in dioxane. (4b) is obtained in the form of a white powder (12 mg, 86%).

$R_f$=0.35 ($CH_2Cl_2$/MeOH: 9/1); MS: FAB>0 (GT): 665: $(M+H)^+$; $^{31}P$ NMR (DMSO-$d_6$): δ=28.09 and 28.22 ppm; $^1H$ NMR (DMSO-$d_6$): δ=11.34 (2s, 2H, 2NH); 7.68 and 7.48 (2d, 2H, $2H_6$); 6.20 (t, 2H, $2H_{1'}$); 5.48 (d, 1H, $OH_{3'}$), 5.26 (pq, 1H, $OH_{5'}$), 5.09 (m, 1H, $H_{3'}$ ($N_1$)), 4.26 (m, 3H, $H_{3'}$ ($N_2$), $H_{5'}$ and $H_{5''}$ (N2)); 4.10 (m, 1H, $H_{4'}$ ($N_1$)); 3.95 (m, 1H, $H_{4'}$ ($N_2$)); 3.61 (m, 2H, $H_{5'}$ and $H_{5''}$ ($N_1$)); 3.13 and 3.02 (2m, 4H, $SCH_2CH_2S$); 2.29 (m, 2H, $H_{2'}$ and $H_{2''}$ ($N_1$)); 2.33 (d, 3H, $CH_3CO$); 2.13 (m, 2H, $H_{2'}$ and $H_{2''}$ ($N_2$)); 1.77 and 1.78 (2s, 6H, $2CH_3$ ($N_1$ and $N_2$)) ppm.

EXAMPLE 3

O-[5'-O-(4,4'-Dimethoxytrityl)thymidin-3'-yl] O-[3'-O-(4,4'-dimethoxytrityl) thymidin-5'-yl] S-(acetylthiomethyl) phosphorothioate (3c)

Iodomethylacetyl sulfide (98 mg; 0.457 mmol) is added to a solution of phosphorothioate diester dinucleoside (1) (58 mg; 0.0457 mmol) in anhydrous acetonitrile (5 ml). The reaction is left with stirring all night at ambient temperature, then the reaction mixture is neutralized by addition of a 1M aqueous solution of TEAB (1 ml) and left with stirring for several minutes. The reaction mixture is then poured onto a 0.5M aqueous solution of TEAB (25 ml) and extracted with dichloromethane (3×15 ml). The organic phases are collected, washed with water (25 ml), dried over sodium sulfate, filtered and then evaporated to dryness. The residue is then chromatographed on a column of silica gel using a gradient of methanol (0 to 3%) in dichloromethane as eluent. (3c) is obtained in the form of a white solid (46 mg, 80%).

$R_f$=0.55 ($CH_2Cl_2$/MeOH: 9/1).

O-(Thymidin-3'-yl) O-(thymidin-5'-yl) S-(acetylthiomethyl) phosphorothioate (4c)

The totally protected phosphorothioate dinucleoside (3c) is dissolved in an acetic acid/water/methanol mixture (8:1:1, v:v:v) (5 ml) and left with stirring at ambient temperature all night. The following day, the reaction mixture is evaporated and coevaporated several times with water and with toluene. The residue is then chromatographed on a column of silica gel using a gradient of methanol (0 to 10%) as eluent. The fractions containing the detritylated phosphorothioate triester dinucleoside (4c) are collected and concentrated under reduced pressure. The residue is coevaporated with dioxane and then lyophilized in dioxane. (4c) is obtained in the form of a white powder (20 mg, 85%).

$R_f$=0.62 ($CH_2Cl_2$/MeOH: 8/2); MS: FAB>0 (GT): 651 $(M+H)^+$; $^{31}P$ NMR ($CD_3CN$): δ=27.22 and 27.44 ppm (2 diastereoisomers); $^1H$ NMR (DMSO-$d_6$): δ=11.34 (d, 2H, 2 NH); 7.70 and 7.49 (2d, 2H, $2H_6$); 6.22 (m, 2H, $2H_{1'}$); 5.48 (d, 1H, $OH_{3'}$); 5.37 (m, 1H, $OH_{5'}$); 5.08 (m,1H, $H_{3'}$ ($N_1$)); 4.29 (m, 5H, $H_{3'}$ ($N_2$), $H_{5'}$ and $H_{5''}$ ($N_2$), $SCH_2S$); 4.13 (m, 1H, $H_{4'}$ ($N_1$)); 3.97 (m, 1H, $H_{4'}$ ($N_2$)); 3.62 (m, 2H, $H_{5'}$ and $H_{5'}$ ($N_1$)), 2.39 (m, 5H, $H_{2'}$ and $H_{2''}$ ($N_1$), $CH_3CO$), 2.15 (m, 2H, $H_{2'}$ and $H_{2''}$ ($N_2$)); 1.78 (s, 6H, $2CH_3$ ($N_1$ and $N_2$)).

I-2—Stability studies on dimeric phosphorothioate triesters 4a, 4b and 4c

General conditions

Method

The stability of the dimers (4a), (4b) and (4c) in different biological media were studied according to an HPLC technique perfected in the laboratory (A. Pompon, I. Lefebvre, J. L. Imbach, *Biochemical Pharmacology* 43, 1769 (1992)), which does not require any preliminary handling of the sample and allows its direct injection; a precolumn, which allows proteins to be eliminated, filled with a new material ISRP (Internal Surface Reverse Phase) is combined with a high resolution column (inverse phase) allowing chromatographic analysis.

Equipment

The chromatograph (Waters-Millipore) is composed of:
- an M 680 programmer
- two M 510 pumps
- a WISP 712 automatic injector
- an M 990 UV diode array detector
- an NEC APC IV microcomputer
- a Waters 990 printer
- a model 7010 6-way valve (Rheodyne).

The columns are supplied by SFCC Shandon:
- ISRP precolumn (Ultrabiosep $C_{18}$, 10 µm, 4.6 mm×10 mm)
- Inverse phase analytical column (Nucleosil C18, 5 µm, 4.6 mm×100 mm) The analytical column is thermostatted at 30° C.

The analysis of the results is carried out on the EUREKA software.

Chemical products

Distilled water is purified on a MilliQ system (Waters-Millipore), Acetonitrile is of HPLC-far UV quality (Fisons), Ammonium acetate is of "analytical" quality (MERCK), The culture media are composed of 90% of RPMI 1640 and 10% of heat-inactivated fetal calf serum (GIBCO), The cellular extracts were kindly supplied by Miss A. -M. Aubertin (University of Strasbourg I). They are prepared in the following way: CEM cells in the exponential growth phase are separated from the culture medium by centrifugation ($10^4$ g, 4 min, 40°). The residue (approximately 100 µl, $5 \times 10^7$ cells) is dissolved in 2 ml of buffer (Tris-HCl 140 mM, pH=7.4) and sonicated. The lysate is centrifuged ($10^5$ g, 1 h, 4°) to eliminate membranes, organelles and chromatin. Two types of eluents were utilized for the HPLC:
- eluent A: 0.1M ammonium acetate buffer, pH=5.9,
- eluent B: 0.1M ammonium acetate buffer, 50% acetonitrile, pH=5.9.

Preparation of the samples

A $10^{-2}$M solution of the compound to be studied is prepared in DMSO.

This solution is diluted with water to give a parent solution of concentration $5 \times 10^{-4}$M.

a) Study of stability in culture medium:

100 µl of parent solution of the compound to be studied are added to 900 µl of culture medium which has previously been filtered on a Millex GV sterile filter (Millipore, 0.22 µm). After mixing, fractions (100 µl) are distributed in sterile Eppendorf tubes. These tubes are placed in an oven at 37° C. and removed as a function of the kinetic development. The samples are immediately analyzed by HPLC (volume injected: 80 µl) or preserved at −25° C. with a view to subsequent analysis.

b) Study of stability in cellular extract: 100 µl of parent solution of the compound to be studied are added to 900 µl of cellular extract which has previously been filtered on a Millex GV sterile filter (Millipore, 0.22 µm). After mixing, fractions (100 µl) are distributed in Eppendorf tubes. These tubes are placed in an oven at 37° C. and removed as a function of the kinetic development. The samples are immediately analyzed by HPLC.

Results

The results regarding the stability studies of the three dimers (4a), (4b) and (4c) are collected in the table below:

$C_0 = 5 \times 10^{-5}$M $t_{1/2}$ = time at the end of which half of the starting product has decomposed $PO^-$ = phosphodiester dinucleoside $PS^-$ = phosphorothioate diester dinucleoside % $PO^-$, % $PS^-$ = molar fractions of phosphodiester dinucleoside and of phosphorothioate diester dinucleoside, expressed in relation to the initial quantity of phosphorothioate triester dinucleoside.

The percentage of $PS^-$ corresponds to the quantity of phosphorothioate diester dinucleoside formed after complete decomposition of the starting phosphorothioate triester dinucleoside (considering that the phosphorothioate diester dinucleoside is stable under the condition used and accumulates).

The percentage of $PO^-$ is calculated by the difference (100−% $PS^-$ formed) because the phosphodiester dinucleoside decomposes rapidly from its formation.

|  | RPMI + 10% serum | | | cellular extract | | |
| --- | --- | --- | --- | --- | --- | --- |
|  | $t_{1/2}$ | % $PO^-$ | % $PS^-$ | $t_{1/2}$ | % $PO^-$ | % $PS^-$ |
| (4a) | 6 h | 80 | 20 | 40 min | / | 100 |
| (4b) | 7 h | 50 | 50 | 10 min | / | 100 |
| (4c) | 1 h | 20 | 80 | 5–10 min | / | 100 |

It follows from the stability study of the compounds 4a–c presented above that these are rapidly and selectively converted in cellular extract into their corresponding phosphorothioate diester, which is in agreement with the original hypothesis.

II—Examples 4 to 6: Synthesis of oligonucleotides containing phosphorothioate triester bonds by postsynthesis alkylation of phosphorothioate diester bonds. Evaluation of their stability in biological media II-1—Synthesis of oligonucleotides 5c, 6b and 7b containing phosphorothioate triester bonds

General conditions

The oligonucleotides containing phosphorothioate diester bonds were synthesized on a solid phase in an Applied Biosystems model 381 A DNA synthesizer, on support columns corresponding to one µmole of grafted nucleoside.

The purification and analysis of the oligonucleotides nucleotides 5c, 6b and 7b were carried out by HPLC using a chromatographic system composed of Waters-Millipore equipment:
- an M 680 programmer
- an NEC APC IV computer
- a Waters 990 printer
- two M 510 pumps
- a $U_6K$ injector
- a UV diode array detector The columns and the precolumns are supplied by SFCC-Shandon:
- in the case of preparative HPLC, a Nucleosil $C_{18}N$ 525 column (10 mm×250 mm) of particle size 5 µm was used, protected by a Nucleosil $C_{18}$PSF-25 precolumn of particle size 5 µm,
- in the case of analytical HPLC, a Nucleosil $C_{18}N$ 125 column (4.6 mm×150 mm) of particle size 5µm protected by a Nucleosil $C_{18}$PSF-25 precolumn of particle size 5 µm used.

After purification, the oligonucleotides are filtered on a Millex HV-13 filter (Millipore, 0.45 µm) and submitted to several successive lyophilizations in water.

Following alkylation reactions of the oligonucleotides and of purification of the alkylated oligonucleotides 5c, 6b and 7b were carried out by HPLC on a Waters-Millipore chromatograph composed of:
- a 600 E programmer
- a 600 pumping system
- a $U_6K$ manual injector After purification by preparative HPLC, we obtained 37 $A_{260}$ units of chimeric oligonucleotide of a spectrophotometric purity of 100% (determined by HPLC analysis).

b)—Alkylation of the phosphorothioate diester bonds.

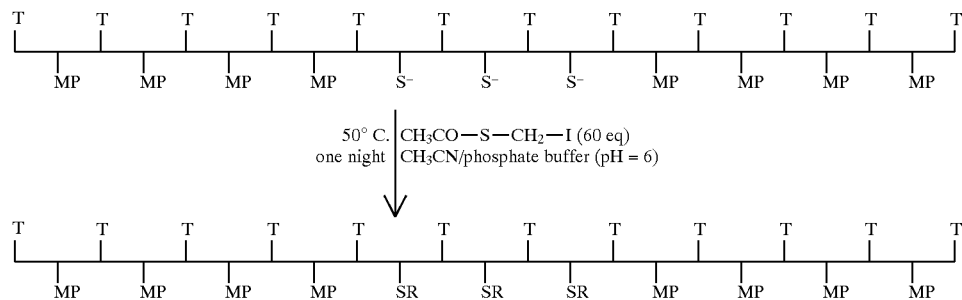

- a 486 UV detector
- a Powermate SX Plus microcomputer.

Follwing of alkylation reactions was carried out on a Nucleosil $C_{18}$ 5 µm column (4.6 mm×150 mm) protected by a Nucleosil $C_{18}$ 5 µm precolumn (SFCC - Shandon).

The purification of the oligonucleotides 5c, 6b and 7b was carried out on a RADIAL-PAK $C_{18}$ 10 µm cartridge to support the RCM column (8×10), protected by a GUARD-PAK Resolve $C_{18}$ precolumn (Waters-Millipore).

The desalting of the samples was carried out on a $C_{18}$ SEP—PAK cartridge (Waters-Millipore).

Before lyophilization, the solutions are filtered on a Millex HV-13 filter (Millipore, 0.45 µm).

II-1-1—EXAMPLE 4
Synthesis of the chimeric dodecamer 5c containing a phosphorothioate triester central window and methylphosphonate flanks a)—Synthesis of a dodecamer containing a phosphorothioate diester central window and methylphosphonate flanks

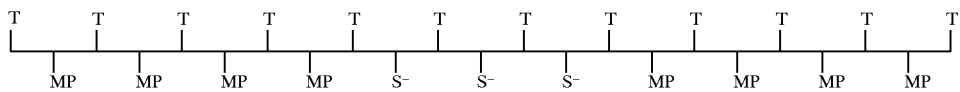

The standard elongation cycle proposed for the synthesis of oligonucleotides was used, using the methylphosphonamidite synthon for the flanks and the mixture $I_2$/THF/water/pyridine as oxidation agent, and the cyanoethyl phosphoramidite synthon and the Beaucage reagent as sulfuration agent (R. P. Iyer, W. Egan, J. B. Regan, S. L. Beaucage, *J. Am. Chem. Soc.*, 112, 1253 (1990)) for the central part (3 incorporation cycles).

The detachment of the oligonucleotide from the support and its deprotection were carried out according to the procedure conventionally described for methylphosphonates (P. S. Miller, M. P. Reddy, A. Murakami, K. R. Blake, S. B. Lin, C. H. Agris, *Biochemistry*, 25, 5092 (1986)) using a solution of ethylenediamine in absolute ethanol (1:1, v:v).

The synthesis on the one micromole scale led us to a rough synthesis figure of 75 absorption units at 260 nm ($A_{260}$ units).

The following are introduced successively into an Eppendorf:
- 120 µl of acetonitrile
- 135 µl of 20 mM phosphate buffer (pH=6.15)
- 15 µl of iodomethylacetyl sulfide in 0.92M solution in acetonitrile
- 30 µl of 7.66 mM solution of oligonucleotide in water (being approximately 22 A26 0 units)

The Eppendorf is placed in a dry bath previously thermostatted at 50° C.

Samples of 5 µl are taken at different reaction times and are analyzed by HPLC in order to estimate the progress of the reaction.

After 16 hours of reaction, the presence of the starting oligonucleotide is no longer detected ($t_r$=12.99 min) and the totally alkylated oligonucleotide ($t_r$=17.53 min) is purified by HPLC.

The oligonucleotide is then desalted, before being lyophilized in a water/dioxane mixture (50:50, v:v) and analyzed again by HPLC.

10 $A_{260}$ units of totally alkylated oligonucleotide of a spectrophotometric purity of 97% were obtained (determined by HPLC).

II-1-2— EXAMPLE 5
Synthesis of the entirely phosphorothioate thioate triester dodecamer 6b a)—Synthesis of a phosphorothioate diester dodecamer $d(C_{P(S)}A_{P(S)}C_{P(S)}C_{P(S)}C_{P(S)}A_{P(S)}A_{P(S)}T_{P(S)}T_{P(S)}C_{P(S)}T_{P(S)}G)$ SEQ. ID. NO: 1, The standard cycle of elongation proposed for the synthesis of oligonucleotides using cyanoethyl phosphoramidite synthons of the four bases suitably protected and replacing the oxidation step with $I_2$/THF/water/pyridine by a sulfuration step with the Beaucage reagent was used.

The detachment of the oligonucleotide from the support and its deprotection were carried out by treatment with concentrated ammonia (32%) overnight at 55° C.
b)—Alkylation of the phosphorothioate diester bonds Phosphate buffer (pH=6.15, 123 µl), acetonitrile (120 µl) and a 1M solution of iodoethylacetyl sulfide (2d) (55 µl) are added successively to a solution of 6.4 mM phosphorothioate diester oligonucleotide, d($C_{P(S)}A_{p(s)}C_{p(s)}C_{p(s)}C_{p(s)}A_{p(s)}A_{p(s)}T_{p(s)}T_{p(s)}C_{p(s)}T_{p(s)}G$) SEQ. ID. NO: 1, in water (42 µl). The mixture is maintained at 50° C. for 48 hours. After evaporation, the residue is purified by HPLC. The fraction containing the completely alkylated phosphorothioate dodecamer 6b is desalted and the evaporation residue taken up again in a water/dioxane mixture (50:50, v:v, 1 ml) is lyophilized.

Yield 35%. Reference (2d) refers to the nomenclature used in the synthesis scheme of the paragraph I-1.

II-1-3—EXAMPLE 6

Synthesis of the chimeric dodecamer 7b containing a central window formed of phosphorothioate triester β-nucleosides and of flanks formed of phosphate diester α-nucleosides.
a)—Synthesis of the dodecamer containing a β-phosphorothioate diester window and of d[α-(TCTT) 3'→3'β-($T_{P(s)}T_{p(s)}C_{p(s)}$C) 5'→5'α-(CTCT)] SEQ. ID. NO: 2α-phosphate diester flanks The standard cycle of elongation proposed for the synthesis of oligonucleotides using α-anomeric cyanoethyl phosphoramidite synthons suitably protected on the bases for the flanks and the mixture $I_2$/THF/water/pyridine as oxidizing agent, and the β-anomeric cyanoethyl phosphoramidite synthons suitably protected on the bases for the central part and the Beaucage reagent as sulfuration agent were used.
b)—Alkylation of the phosphorothioate diester bonds Phosphate buffer (pH=6.15, 145 µl) and a solution of 1M iodoethylacetyl sulfide (2d) (55 µl) are added successively to an 11 mM solution of d[α-(TCTT)3'→3'β-($T_{P(s)}T_{p(s)}C_{p(s)}$C) 5'→5'α-(CTCT)] SEQ. ID. NO: 2oligonucleotide in water (20 µl). The mixture is maintained at 50° C. for 48 hours. After evaporation, the residue is purified by HPLC. The fraction containing the dodecanucleotide (7d) alkylated on the three central phosphorothioate bonds is desalted and then lyophilized. Yield 47%.

II-2—Study of stability of the chimeric oligonucleotides nucleotides 5c, 6b and 7b in biological media.

General conditions

The general conditions are the same as those used for the study of stability of the phosphorothioate triester dimers, as far as the method, the equipment and the chemical products are concerned.

Preparation of the samples

A parent solution of oligonucleotide is prepared in dioxane (10 $A_{260}$ units of oligonucleotide in 200 µl of dioxane).
a)—Study of stability in culture medium:

30 µl of parent solution of oligonucleotide (being approximately 1.5 $A_{260}$ units) are removed, which are added to 1470 µl of culture medium which has previously been filtered on a sterile Millex GV filter (Millipore 0.22 µm). After mixing, fractions (100 µl) are distributed in sterile Eppendorf tubes. These tubes are placed in an oven at 37° C. and removed as a function of the kinetic development. The samples are immediately analyzed by HPLC (volume injected 80 µl) or preserved at -25° C. with a view to subsequent analysis.
b)—Study of stability in cellular extract:

10 µl of oligonucleotide parent solution are added to 990 µl of cellular extract which have previously been filtered on a sterile Millex GV filter (Millipore, 0.22 µm). After mixing, fractions (100 µl) are distributed in sterile Eppendorf tubes, placed in an oven at 37° C., sampled at different times and immediately analyzed by HPLC.

Results

The results regarding the stability studies of the three oligonucleotides 5c, 6b and 7b are collected in the table below.

| | RPMI + 10% serum | | cellular extract |
|---|---|---|---|
| oligo-nucleotide studied | $t_{1/2}$ of disappearance of the starting oligonucleotide | $t_{1/2}$ of disappearance of the starting oligonucleotide | $t_{1/2}$ of formation of the totally deprotected oligonucleotide |
| 5c | 40 min | <5 min | 20 min |
| 6b | 55 min | <2 min | 25 min |
| 7b | 35 min | <2 min | 20 min |

All of the data regarding the compounds 5c, 6b and 7b shows without ambiguity that it is possible to protect internucleotide phosphorothioate functions selectively by bioreversible groups. In addition, it is indeed confirmed in cellular extracts that such phosphorothioate triester oligonucleotides are rapidly deprotected.

FIG. 1 shows the mechanism of decomposition of bioreversible groups according to the invention.

We claim:

1. An oligonucleotide comprising the general formula

 (I)

in which:

Y is O or S;

$R_1$ and $R_2$ are, respectively, a residue in the 3' -O and 5' -O positions of a nucleoside or of an oligonucleotide, the internucleotide linkage of which is natural or modified;

X is —$(CH_2)_n$—S—S—U, —$(CH_2)_n$—O—C(=$Y^2$)—Z or —$(CH_2)_n$—S—C(=O)—Z;

each n is independently an integer from 1 to 6;

U is an optionally substituted alkyl, aryl or sugar residue;

$Y^2$ is O or S; and

Z is optionally substituted alkyl or sugar residue.

2. An oligonucleotide according to claim 1, where n=1 or 2.

3. An oligonucleotide comprising the general formula

 (I)

in which:

Y is O or S;

$R_1$ and $R_2$ are respectively a residue in the 3' -O and 5' -O positions of a nucleoside or of an oligonucleotide, the internucleotide linkage of which is natural or modified;

X is a —$(CH_2)_n$—$Y^1$—W radical, where $y^1$ is S or O;

each n is independently an integer from 1 to 6; and

W is either SU or —C($Y^2$)—Z, where U and Z are a lower alkyl, optionally substituted by one or more groups selected from the group consisting of OH, SH and $NH_2$, and where $Y^2$ is O or S.

4. An oligonucleotide according to claim 1, characterized in that U and Z are a lower alkyl, optionally substituted by one or more groups selected from the group consisting of OH, SH and $NH_2$.

5. An oligonucleotide according to claim 3, characterized in that X is —$(CH_2)_n$—S—S—$(CH_2)_{n1}$—$X^1$, wherein n and $n^1$ are an integer from 1 to 4, and $X^1$ is H, OH, SH or $NH_2$, or X is —$(CH_2)_n$—$Y^1$—C(=O)—Z, where Z=$CH_3$ or tBu.

6. An oligonucleotide according to claim 1, characterized in that it is formed of a chimeric oligomer comprising a central DNA or RNA sequence, the internucleotide linkages of which comprise a

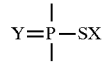

bond, this central sequence being flanked in the 5' and 3' positions by DNA or RNA sequences modified so that they are resistant to nucleases and/or stabilize hybridization with a complementary strand.

7. An oligonucleotide according to claim 1, wherein said internucleotide linkage is a phosphorothioate triester.

8. An oligonucleotide according to claim 3, characterized in that it is formed of a chimeric oligomer comprising a central DNA or RNA sequence, the internucleotide linkages of which comprise a

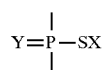

bond, this central sequence being flanked in the 5' and 3' positions by DNA or RNA sequences modified so that they are resistant to nucleases and/or stabilize hybridization with a complementary strand.

9. An oligonucleotide according to claim 5, characterized in that it is formed of a chimeric oligomer comprising a central DNA or RNA sequence, the internucleotide linkages of which comprise a

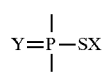

bond, this central sequence being flanked in the 5' and 3' positions by DNA or RNA sequences modified so that they are resistant to nucleases and/or stabilize hybridization with a complementary strand.

10. An oligonucleotide comprising the general formula

 (I)

in which:

Y is O or S;

$R_1$ and $R_2$ are respectively a residue in the 3'-O and 5'-O positions of a nucleoside or of an oligonucleotide, the internucleotide linkage of which is natural or modified;

X is a $-(CH_2)_n-Y^1-W$ radical where
  $Y^1$ is S or O;
  each n is independently an integer from 1 to 6; and
  W is either SU or $-C(Y^2)-Z$, where
    U is an optionally substituted alkyl, aryl or sugar residue;
    $Y^2$ O or S; and
    Z is an optionally substituted alkyl, aryl or sugar residue;

wherein $R_1$ and $R_2$ have electrically neutral sequences at the 5' and 3' ends respectively, which are resistant to degradation by exonucleases; and wherein the internucleotide linkages at the 5' and 3' ends respectively of $R_1$ and $R_2$ are of the methylphosphonate type.

11. An oligonucleotide comprising the general formula

(I)

in which:

Y is O or S;

$R_1$ and $R_2$ are respectively a residue in the 3'-O and 5'-O positions of a nucleoside or of an oligonucleotide, the internucleotide linkage of which is natural or modified;

X is a $-(CH_2)_n-Y^1-W$ radical where
  $Y^1$ is S or O;
  each n is independently an integer from 1 to 6; and
  W is either SU or $-C(Y^2)-Z$, where
    U is an optionally substituted alkyl, aryl or sugar residue;
    $Y^2$ is O or S; and
    Z is an optionally substituted alkyl, aryl or sugar residue;

wherein said oligonucleotide is formed from a chimeric oligomer comprising a β-anomeric central DNA or RNA sequence, the internucleotide linkages of which are of the

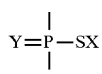

type, this central sequence being flanked in the 5' and 3' positions by α-anomeric DNA or RNA.

12. An oligonucleotide according to claim 1, characterized in that said oligonucleotide is formed from a chimeric oligomer comprising a β-anomeric central DNA or RNA sequence, the internucleotide linkages of which are of the

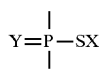

type, this central sequence being flanked in the 5' and 3' positions by α-anomeric DNA or RNA.

13. An oligonucleotide according to claim 11, characterized in that it is formed from a chimeric oligomer containing a surrounding central sequence of phosphorothioate triester β-nucleoside with internucleotide linkage of the

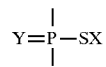

type, surrounded by flanks formed from phosphate diester alpha-nucleoside linkages.

14. An oligonucleotide according to claim 12, characterized in that it is formed from a chimeric oligomer containing a surrounding central sequence of phosphorothioate triester β-nucleosides with internucleotide linkage of the

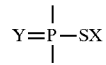

type, surrounded by flanks formed from phosphate diester alpha-nucleoside linkages.

15. A method of preparing an oligonucleotide comprising the general formula

(I)

in which:

Y is O or S;

$R_1$ and $R_2$ are respectively a residue in the 3'-O and 5'-O positions of a nucleoside or of an oligonucleotide, the internucleotide linkage of which is natural or modified;

X is a $-(CH_2)_n-Y^1-W$ radical where
  $Y^1$ is S or O;
  each n is independently an integer from 1 to 6; and
  W is either SU or $-C(y^2)-Z$, where
    U is an optionally substituted alkyl, aryl or sugar residue;
    $Y^2$ is O or S; and
    Z is an optionally substituted alkyl, aryl or sugar residue;

wherein a nucleophilic substitution reaction by the sulfur atom of the $-P-S$ bond of a phosphorothioate diester oligonucleotide is carried out on an alkylating agent XL, thus leading to the formation of

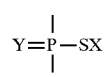

phosphorothioate triester linkages, L being a leaving group such as halogen, ester or tosyl, and X being a bioreversible group such as defined in claims 1 to 13.

16. A method of preparing an oligonucleotide according to claim 1, characterized in that a nucleophilic substitution reaction by the sulfur atom of the $-P-S$ bond of a phosphorothioate diester oligonucleotide is carried out on an alkylating agent XL, thus leading to the formation of

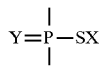

phosphorothioate triester linkages, L being a leaving group such as halogen, ester or tosyl, and X being a bioreversible group such as defined in claims 1 to 14.

17. An oligonucleotide according to claim 1, characterized in that U and Z are a lower alkyl, optionally substituted by one or more groups chosen from amongst OH, SH and $NH_2$.

18. An oligonucleotide according to claim 2, characterized in that U and Z are a lower alkyl, optionally substituted by one or more groups chosen from amongst OH, SH and $NH_2$.

19. An oligonucleotide according to claim 1, characterized in that $R_1$ and $R_2$ have electrically neutral sequences at the 5' and 3' ends respectively, which are resistant to degradation by exonucleases.

20. An oligonucleotide according to claim 2, characterized in that $R_1$ and $R_2$ have electrically neutral sequences at the 5' and 3' ends respectively, which are resistant to degradation by exonucleases.

21. An oligonucleotide according to claim 3, characterized in that $R_1$ and $R_2$ have electrically neutral sequences at the 5' and 3' ends respectively, which are resistant to degradation by exonucleases.

22. An oligonucleotide according to claim 5, characterized in that $R_1$ and $R_2$ have electrically neutral sequences at the 5' and 3' ends respectively, which are resistant to degradation by exonucleases.

23. An oligonucleotide comprising the general formula

   (I)

in which:
  Y is O or S;
  $R_1$ and $R_2$ are respectively a residue in the 3'-O and 5'-O positions of a nucleoside or of an oligonucleotide, the internucleotide linkage of which is natural or modified;
  X is a —$(CH_2)_n$—$Y^1$—W radical where
    $Y^1$ is S or O;
    each n is independently an integer from 1 to 6; and
    W is either SU or —$C(Y^2)$—Z, where
      U is an optionally substituted alkyl, aryl or sugar residue;
      $Y^2$ O or S; and
      Z is an optionally substituted alkyl, aryl or sugar residue;
  characterized in that said oligonucleotide is formed from a chimeric oligomer comprising a beta-anomeric central DNA or RNA sequence, the internucleotide linkages of which have the formula

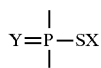

this central sequence being flanked in the 5' and 3' positions by alpha-anomeric DNA or RNA.

24. An oligonucleotide according to claim 1, characterized in that it is formed from a chimeric oligomer comprising a beta-anomeric central DNA or RNA sequence, the internucleotide linkages of which have the formula

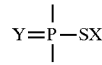

this central sequence being flanked in the 5' and 3' positions by alpha-anomeric DNA or RNA.

25. An oligonucleotide according to claim 2, characterized in that it is formed from a chimeric oligomer comprising a beta-anomeric central DNA or RNA sequence, the internucleotide linkages of which have the formula

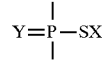

this central sequence being flanked in the 5' and 3' positions by alpha-anomeric DNA or RNA.

26. An oligonucleotide according to claim 3, characterized in that it is formed from a chimeric oligomer comprising a beta-anomeric central DNA or RNA sequence, the internucleotide linkages of which have the formula

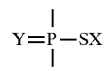

this central sequence being flanked in the 5' and 3' positions by alpha-anomeric DNA or RNA.

27. An oligonucleotide according to claim 5, characterized in that it is formed from a chimeric oligomer comprising a beta-anomeric central DNA or RNA sequence, the internucleotide linkages of which have the formula

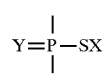

this central sequence being flanked in the 5' and 3' positions by alpha-anomeric DNA or RNA.

28. An oligonucleotide according to claim 1, characterized in that it is formed from a chimeric oligomer comprising a beta-anomeric central DNA or RNA sequence, the internucleotide linkages of which have the formula

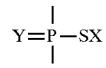

this central sequence being flanked in the 5' and 3' positions by alpha-anomeric DNA or RNA.

29. A phosphorothioate triester oligonucleotide comprising internucleotide linkages which have a P—S bond wherein the S moiety thereof is protected by a group comprising a carbonyl-containing moiety; and
  wherein said carbonyl-containing moiety is of the formula —$(CH_2)_n$—$Y^1$—W wherein:
    $Y^1$ is S or O;
    each n is independently an integer from 1 to 6; and
    W is -$C(Y^2)Z$ where $Y^2$ is O or S; and
    Z is optionally substituted alkyl or a sugar residue.

30. An oligonucleotide according to claim 29 wherein $Y^1$ is O.

31. An oligonucleotide according to claim 29 wherein $Y^2$ is O.

32. An oligonucleotide according to claim 29 wherein Z is optionally substituted alkyl.

33. An oligonucleotide according to claim 29 having 5 to 50 nucleotides.

34. An oligonucleotide comprising the general formula $$R_1-\overset{\overset{X}{\|}}{\underset{SX}{P}}-R_2 \qquad (I)$$

in which:

Y is O;

$R_1$ and $R_2$ are, respectively, a residue in the 3'-O and 5'-O positions of a nucleoside or of an oligonucleotide, the internucleotide linkage of which is natural or modified;

X is $-(CH_2)_n-S-S-U$, $-(CH_2)_n-O-C(=Y^2)-Z$ or $-(CH_2)_n-S-C(=O)-Z$;

each n is independently an integer from 1 to 6;

U is an optionally substituted alkyl, aryl or sugar residue;

$Y^2$ is O or S; and

Z is optionally substituted alkyl, aryl or sugar residue.

35. An oligonucleotide comprising the general formula $$R_1-\overset{\overset{X}{\|}}{\underset{SX}{P}}-R_2 \qquad (I)$$

in which:

Y is O or S;

$R_1$ and $R_2$ are, respectively, a residue in the 3'-O and 5'-O positions of a nucleoside or of an oligonucleotide, the internucleotide linkage of which is natural or modified;

X is $-(CH_2)_n-S-S-U$ or $-(CH_2)_n-O-C(=Y^2)-Z$;

each n is independently an integer from 1 to 6;

U is an optionally substituted alkyl, aryl or sugar residue;

$Y^2$ is O or S; and

Z is optionally substituted alkyl, aryl or sugar residue.

* * * * *

UNITED STATES PATENT AND TRADEMARK OFFICE
CERTIFICATE OF CORRECTION

PATENT NO.   : 5,770,713
DATED        : June 23, 1998
INVENTOR(S)  : Jean-Louis Imbach et al.

It is certified that error appears in the above-identified patent and that said Letters Patent is hereby corrected as shown below:

Column 2,
Line 57, delete "phophorothioate" and insert therefor -- phosphorothioate --.

Column 3,
Line 42, delete "X" in Figure and insert therefor "Y"
Line 62, delete "$y^1$" and insert therefor -- $Y^1$ --.

Column 4,
Line 6, delete "$y^2$" and insert therefor -- $Y^2$ --.
Line 23, delete "$Y^2$" and insert therefor -- $Y^2$ --.

Column 10,
Line 49, delete "$H_5$'" and insert therefor -- $H_{5''}$ --.

Column 11,
Line 31, delete "40°'" and insert therefor -- 4° --.

Column 14,
Line 31, delete "A26 0" and insert therefor -- $A_{260}$ --.

Claims 1, 2, 10, 11, 15, 23, and 35,
Change "X" at the beginning of the formula to -- Y --.

UNITED STATES PATENT AND TRADEMARK OFFICE
CERTIFICATE OF CORRECTION

PATENT NO.    : 5,770,713
DATED         : June 23, 1998
INVENTOR(S)   : Jean-Louis Imbach et al.

It is certified that error appears in the above-identified patent and that said Letters Patent is hereby corrected as shown below:

<u>Column 17,</u>
Line 54, delete "$y^1$" and insert therefor -- $Y^1$ --.

<u>Column 20,</u>
Line 43, delete "$(y^2)$" and insert therefor -- $(Y^2)$. --

Signed and Sealed this

Second Day of October, 2001

*Attest:*

*Nicholas P. Godici*

NICHOLAS P. GODICI
*Attesting Officer*    *Acting Director of the United States Patent and Trademark Office*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 12 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

CACCCAATTC TG                                                                                            1 2

( 2 ) INFORMATION FOR SEQ ID NO:2:

( i ) SEQUENCE CHARACTERISTICS:
        ( A ) LENGTH: 12 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

TCTTTTCCCT CT                                                                                            1 2